US010293068B2

(12) United States Patent
Ruley et al.

(10) Patent No.: US 10,293,068 B2
(45) Date of Patent: May 21, 2019

(54) METHOD AND DEVICE FOR HYDROGEN PEROXIDE STERILIZATION

(71) Applicant: STERIS EUROPE, INC. SUOMEN SIVULIIKE, Tuusula (FI)

(72) Inventors: Arja Ruley, Espoo (FI); Mauri Salmisuo, Tuusula (FI)

(73) Assignee: STERIS EUROPE, INC. SUOMEN SIVULIIKE, Tuusula (FI)

( * ) Notice: Subject to any disclaimer, the term of this patent is extended or adjusted under 35 U.S.C. 154(b) by 186 days.

(21) Appl. No.: 15/014,357

(22) Filed: Feb. 3, 2016

(65) Prior Publication Data

US 2016/0235877 A1 Aug. 18, 2016

(30) Foreign Application Priority Data

Feb. 13, 2015 (EP) ..................................... 15397506

(51) Int. Cl.
*A61L 2/20* (2006.01)
(52) U.S. Cl.
CPC ......... *A61L 2/208* (2013.01); *A61L 2202/122* (2013.01); *A61L 2202/15* (2013.01)
(58) Field of Classification Search
CPC ...................................................... A61L 2/208
USPC ......................................................... 422/33
See application file for complete search history.

(56) References Cited

U.S. PATENT DOCUMENTS

2003/0127506 A1* 7/2003 Braun, Jr. ................. A61L 2/10
232/31
2005/0084415 A1* 4/2005 McVey .................... A61L 2/186
422/28
2008/0206119 A1* 8/2008 Habrovec ................. A61L 2/07
422/295
2013/0004380 A1 1/2013 Yoo .............................. 422/186
2014/0037496 A1* 2/2014 Pomeroy ................. A61L 2/208
422/3
2016/0193375 A1* 7/2016 Laflamme ................. A61L 2/24
422/33

FOREIGN PATENT DOCUMENTS

WO WO 97/25075 7/1997 ............... A61L 2/20

OTHER PUBLICATIONS

Jones et al., Using hydrogen peroxide vapor to decontaminate biological safety cabinets, 1993, The Baker Company, vol. 1 No. 1 of Acumen publication, pp. 1-2.*
Search Report issued in corresponding European Patent Application No. 15397506.5, dated Jul. 27, 2015.
Office Action issued in corresponding Canadian Patent Application No. 2,919,934 dated Feb. 28, 2017.

* cited by examiner

*Primary Examiner* — Kevin Joyner
*Assistant Examiner* — Holly M Mull
(74) *Attorney, Agent, or Firm* — Kusner & Jaffe

(57) ABSTRACT

The invention relates to the sterilization of a load of goods with hydrogen peroxide vapor in a closed space. The method involves a sequence of creating a sub-atmospheric pressure in a sterilization chamber, introduction of vaporized hydrogen peroxide and the use of a gas circulation device within the sterilization chamber, whereby the output of the gas circulation device is controlled according to the pressure in the sterilization chamber. A uniform and consistent distribution of hydrogen peroxide throughout the load is achieved.

6 Claims, 1 Drawing Sheet

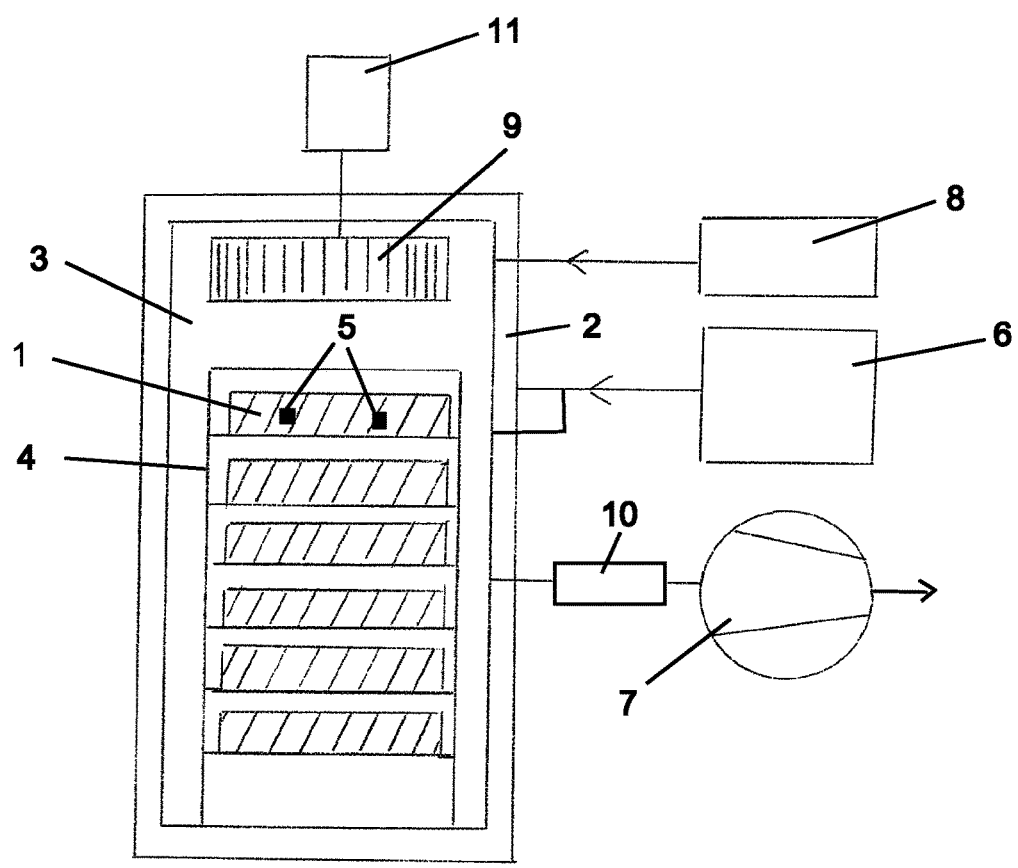

METHOD AND DEVICE FOR HYDROGEN PEROXIDE STERILIZATION

RELATED APPLICATIONS

This application claims the benefit of European Patent Application No. 15397506.5, filed Feb. 13, 2015.

FIELD OF THE INVENTION

The invention relates to the sterilization of a load of goods with hydrogen peroxide vapor in a closed space. In particular, the invention relates to a rapid and effective process for carrying out such a sterilization procedure, with consistent and even distribution of sterilant throughout the load, and with rapid and thorough outgassing of the sterilant after the sterilization cycle has been finished, and to an apparatus for carrying out the process.

BACKGROUND OF THE INVENTION

Gaseous sterilants are typically used for goods for which simple heat sterilization is not appropriate. For example, products containing heat-sensitive biological material in aqueous solution or in dry form, require sterilization at relatively moderate temperatures due to the thermal sensitivity of the materials involved. Packages containing proteins, steroids and vaccine components are examples. In such cases, the use of vacuum, steam and a gaseous sterilant is often an adequate solution. Gaseous sterilants in use include ethylene oxide, formaldehyde, peracetic acid and hydrogen peroxide. Ethylene oxide and formaldehyde are considered to be carcinogenic. Hydrogen peroxide is highly effective and has the advantage that its decomposition products are the relatively harmless substances oxygen and water.

Vaporized hydrogen peroxide (VHP) is used for decontamination and sterilization of enclosed and sealed areas. It is capable of destroying all forms of microbial life, including bacteria, bacterial spores, fungi, fungal spores, and viruses. It is commonly produced from a solution of liquid $H_2O_2$ and water, by means of generators specifically designed for the purpose. Aqueous hydrogen peroxide may be supplied as a 35% stabilized solution, for example Vaprox® supplied by STERIS Corporation.

VHP is used for loads that may be structurally fairly complex, containing voids or spaces. The loads often have low thermal conductivity, e.g. certain polymers. In these cases, uniform distribution of sterilant and temperature is of great importance.

BACKGROUND ART

In the International patent application published as WO 2010/000022 is disclosed a method of sterilizing objects using a sterilizing mist, e.g. hydrogen peroxide. The mist is delivered to a sterilization chamber and allowed to contact the objects for a given duration; subsequently the sterilizing mist is displaced by a gas flow which during a given period removes possibly condensed mist from the object. The reduction in microorganisms for this cycle is less than log 6, and the cycle is repeated until a predetermined sterilization parameter is achieved. The process is preferably carried out at atmospheric pressure or above.

In the International patent application published as WO 2008/134290, a decontamination system utilizing vaporized hydrogen peroxide is disclosed. The system is provided with a controller for modifying the concentration of the vaporized decontaminant in the relevant space in response to operating conditions, thereby preventing condensation of the vaporized decontaminant during a cycle; i.e. the decontamination system can operate at an optimal concentration level while maintaining a dew point margin.

In European patent application No. 01930156.3 is disclosed a process using gaseous hydrogen peroxide for sterilizing sealing members like elastomer stoppers. The cycle involves a vacuum stage, introduction of gaseous hydrogen peroxide and a hold period, a period of clean gas pressure to cause penetration of hydrogen peroxide into the material; and a number of aeration pulses.

In the International patent application published as WO 97/25075 is disclosed a method for sterilization of articles using hydrogen peroxide, in which method the treatment with sterilant at sub-atmospheric pressure is followed by a sequence of warm steam pulses at a higher pressure, causing rapid outgassing of the hydrogen peroxide absorbed on the articles. Thus, the process is shortened since outgassing to an acceptable level may take a significant amount of time without steam pulsing.

SUMMARY OF THE INVENTION

In particular when the load is prone to absorb sterilant, the concentration of hydrogen peroxide tends to rise at the edges of the load. The concentration of hydrogen peroxide can be monitored using standardized indicator devices which are placed at selected locations in the load. It has been shown, that with prior art methods where e.g. VHP is introduced into an evacuated sterilizer chamber and a hold period follows, a gradient of hydrogen peroxide concentration is formed, the concentration being excessively high at the periphery of the load while the concentration at the center may still be insufficient for proper sterilization. Excessive concentration of sterilant may lead to excessive absorption of sterilant into the material, leading in turn to problems with residual, slowly desorbing toxic substances and prolonged processing periods.

According to the present invention, an improved method is provided for the reliable and repeatable sterilization of loads having a complicated structure and absorbing characteristics, using vaporized hydrogen peroxide and steam and enhanced gas circulation within the sterilization chamber. Excessive use of sterilant may thus be avoided.

The method involves a sequence of creating a sub-atmospheric pressure in a sterilization chamber, introduction of VHP and the use of a gas circulation device within the sterilization chamber whereby the output of the gas circulation device is controlled according to the pressure prevailing in the sterilization chamber.

According to a first aspect of the present invention, a method for sterilizing a load of goods is provided comprising the following steps: a sterilization chamber is charged with a load of goods to be sterilized; the chamber is evacuated to a minimum pressure determined by the characteristics of the load; an atmosphere of vaporized hydrogen peroxide is introduced in an amount determined by the desired final concentration throughout the load; the resulting sterilizing atmosphere is circulated within the chamber at a flow rate determined by the prevailing pressure using a gas circulation device internal to the chamber; and the sterilizing atmosphere is removed.

According to a further aspect of the invention, an apparatus is provided for carrying out the method according to the invention, the apparatus comprising: A chamber for receiving a load of goods to be sterilized, said chamber having a jacket for a heat transfer medium as well as gas inlets and gas outlets; a device for delivering a heat-controlled heat transfer medium to the jacket; within the chamber, a gas circulation device capable of delivering a constant volume flow at variable velocities; a device for producing vaporized hydrogen peroxide: and a device for producing sub-atmospheric pressures within the chamber.

The apparatus further comprises at least one sensor for measuring temperature and at least one sensor for measuring humidity within the chamber, and optionally one or more sensors for measuring hydrogen peroxide concentration at selected points.

The apparatus may also comprise a device or devices for introducing pressurized steam and/or air to the chamber.

BRIEF DESCRIPTION OF THE DRAWINGS

The invention is described in further detail with reference to FIG. 1, showing a schematic drawing of the main components of an apparatus according to the invention.

DETAILED DESCRIPTION OF THE PREFERRED EMBODIMENTS

With reference to FIG. 1, chamber 3, built according to standards for vacuum use is arranged for receiving a load. The load may be arranged on a rack or racks 4 designed for easy handling of various types of goods, which are typically packed in plastic covers, e.g. Tyvek®. The load on the uppermost shelf of the rack is indicated by reference number 1, the lower shelves are loaded similarly but reference numbers are omitted.

The temperature in the chamber is preferably controlled by means of a heat transfer medium generated in heater 6 and circulated through a jacket 2 provided on the chamber walls. Preferably, the heat transfer medium is steam. At the beginning of a sterilization cycle, the sterilization chamber is charged with a load of goods to be sterilized. Indicators of hydrogen peroxide exposure, e.g. as provided by the STERIS corporation, are placed at representative locations throughout the load, as shown in an exemplary manner by reference number 5, in particular when a new type of load is being treated. Loads for which hydrogen peroxide sterilization are suited are usually heat sensitive, and the temperatures used in the process may range from room temperature to about 40° C. Preferably, the load is heated to the predetermined operating temperature by circulating dry air within the chamber while the chamber walls are heated by providing steam to the jacket.

Following a possible preheating as explained, the chamber is evacuated using pump 7 to a minimum pressure determined by the characteristics of the load. This minimum pressure may be as low as 1 mbar, typically about 4 mbar. An atmosphere of vaporized hydrogen peroxide (VHP) produced in generator 8 in a manner known as such is then introduced to the chamber 3. A typical pressure after charging VHP in this case is in the range 20-35 mbar.

According to the present invention, the VHP is preferably charged to the chamber based on a measurement of humidity. The initial evacuation of the chamber is carried out according to the minimum pressure that is acceptable for the current load.

The charged amount of VHP may be monitored using humidity sensors. When measuring the humidity of a VHP atmosphere generated in an evacuated space, the impact of the hydrogen peroxide must be taken into account. The ratio of hydrogen peroxide and water determines the saturation vapor pressure of the gas mixture. Sensors capable of measuring the humidity of such a mixed atmosphere are available, e.g. from the Vaisala corporation. A percentage reading indicating the VHP saturation rate is obtained. The practical operational pressure when VHP saturation humidity is used as a parameter is no higher than 100 mbar, and percentage readings in the range of 60 to 85 are typical.

The humidity readings may thus be correlated to the VHP concentration while dew point conditions are avoided. At suitable humidity levels, a pressure of 10 to 65, preferably 15 to 40, most preferably 20 to 35 mbar above the initial minimum pressure is typically reached.

Hydrogen peroxide concentration sensors can be provided as desired for reference. The final proof of sufficient and consistent hydrogen peroxide concentration is obtained via the mentioned indicators 5 within the load.

In the chamber, preferably in the roof of the chamber, a gas circulation device 9 is provided having a variable speed drive 11 and being capable of providing a constant volume flow regardless of gas density. Preferably this is a mechanical fan, e.g. a centrifugal fan. When the selected humidity is reached, a sterilization phase is initiated. During this phase, the output of the gas circulation device is preferably controlled to be inversely proportional to the pressure in the chamber. Thus, at a low pressure, a high rate of gas circulation is provided. For example, at a hydrogen peroxide/water vapor pressure of 20 to 35 mbar, the output should correspond to at least ½ times the chamber volume per second to ensure uniform distribution of hydrogen peroxide throughout the load. As another example, at a pressure of 500 mbar, the output of the gas circulation device should correspond to ⅓ of the chamber volume per second. "Chamber volume" refers to the volume of the empty sterilization chamber, without load.

Drain connections (not shown) are provided in the chamber 3 and jacket 2 as required.

Appropriate control equipment and instrumentation, such as controllers, temperature and pressure sensors and required valves for automating the processes carried out in the apparatus are provided as contemplated by the skilled person, but not shown in FIG. 1.

The period necessary for obtaining a desired concentration of hydrogen peroxide throughout the load may be determined and validated empirically using hydrogen peroxide indicators as explained above. The time used for the sterilization phase may be in the range of 0.5 to 1 h for a chamber with a volume of 2 m$^3$.

When the sterilization phase is finished, the hydrogen peroxide-containing atmosphere is preferably displaced using steam at a temperature not exceeding the maximum allowed temperature for the specific load.

The effective use of a gas circulation device internal to the chamber during the VHP treatment period ensures the uniform distribution of sterilant throughout the load, compared to prior art methods using sub-atmospheric pressure and a static sterilant atmosphere; or processes using atmospheric or near atmospheric pressure and the sterilant feed is arranged in an external loop including a blower, whereby VHP enters the chamber from the external loop through an inlet and leaves the chamber through an outlet into the loop.

Preferably, an outgassing cycle as disclosed in WO97/25075, hereby incorporated by reference, is applied to remove hydrogen peroxide absorbed into the material of the load. This procedure involves admitting steam to the chamber raising the pressure significantly, and possibly raising the pressure further using air. The temperature may also be raised according to the specifications of the load. Subsequently, the chamber is evacuated, again according to the tolerances of the load, and the cycle is repeated until an acceptable level of residual hydrogen peroxide is achieved. The process is enhanced using the gas circulation device 9 internal to the chamber. Typically, a sequence of five steam pressure-vacuum cycles may be used for sufficient outgassing. The apparatus is equipped with a catalytic destroyer 10 of leaving hydrogen peroxide, for decomposing the hydrogen peroxide to water and oxygen as known in the art.

Having described the invention, the following is claimed:

1. A method for sterilizing a load of goods, comprising:
   charging a sterilization chamber with a load of goods to be sterilized;
   evacuating the chamber to a minimum pressure determined by characteristics of the load;
   introducing to the chamber a sterilizing atmosphere of vaporized hydrogen peroxide based on a humidity of the sterilizing atmosphere measured within the chamber until the measured humidity indicates that a desired final concentration of the sterilizing atmosphere has been reached throughout the load;
   conducting a sterilization within the chamber when the measured humidity indicates that the desired final concentration of the sterilizing atmosphere has been reached throughout the load, the sterilization being conducted at a pressure prevailing in the chamber when the desired final concentration of the sterilizing atmosphere has been reached throughout the load, the conducting comprising controlling an output of a gas circulation device internal to the chamber to circulate the sterilizing atmosphere at the desired final concentration within the chamber at a constant flow rate dictated by the prevailing pressure; and
   after the sterilization, removing the sterilizing atmosphere from the chamber.

2. The method according to claim 1, wherein the prevailing pressure dictates the constant flow rate to be ½ of the chamber volume per second.

3. The method according to claim 1 or 2, wherein the sterilization is followed by an outgassing process involving repeated application of steam pressure and subsequent subatmospheric pressure.

4. A method according to claim 1, further comprising, after the charging the sterilization chamber and before the evacuating the chamber, preheating the load to a predetermined operating temperature.

5. A method according to claim 4, wherein the preheating the load comprises circulating dry air within the chamber while walls of the chamber are heated by steam circulating through a jacket provided on the chamber walls.

6. A method according to claim 1, wherein, during the sterilization, the constant flow rate is inversely proportional to the prevailing pressure.

* * * * *